(12) United States Patent
Ross et al.

(10) Patent No.: US 8,636,696 B2
(45) Date of Patent: Jan. 28, 2014

(54) TRANSDERMAL DEVICE CONTAINING MICRONEEDLES

(75) Inventors: Russell Frederick Ross, Atlanta, GA (US); Andrew Baker, Norcross, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 206 days.

(21) Appl. No.: 13/157,412

(22) Filed: Jun. 10, 2011

(65) Prior Publication Data
US 2012/0316503 A1    Dec. 13, 2012

(51) Int. Cl.
*A61M 5/00* (2006.01)

(52) U.S. Cl.
USPC ........................ 604/173; 604/93.01

(58) Field of Classification Search
USPC .............. 604/173, 272, 93.01, 264; 606/167, 606/172, 181, 183, 184–185
See application file for complete search history.

(56) References Cited

U.S. PATENT DOCUMENTS

| | | | |
|---|---|---|---|
| 3,964,482 A | 6/1976 | Gerstel et al. | |
| 5,279,544 A | 1/1994 | Gross et al. | |
| 5,800,420 A | 9/1998 | Gross et al. | |
| 5,928,207 A | 7/1999 | Pisano et al. | |
| 5,957,895 A | 9/1999 | Sage et al. | |
| 6,132,755 A | 10/2000 | Eicher et al. | |
| 6,375,978 B1 | 4/2002 | Kleiner et al. | |
| 6,623,457 B1 | 9/2003 | Rosenberg | |
| 6,656,147 B1 | 12/2003 | Gertsek et al. | |
| 6,767,341 B2 | 7/2004 | Cho | |
| 6,881,203 B2 | 4/2005 | Delmore et al. | |
| 6,908,453 B2* | 6/2005 | Fleming et al. | 604/173 |
| 6,980,855 B2 | 12/2005 | Cho | |
| 7,047,070 B2 | 5/2006 | Wilkinson et al. | |
| 7,048,723 B1 | 5/2006 | Frazier et al. | |
| 7,131,987 B2* | 11/2006 | Sherman et al. | 604/290 |
| 7,285,113 B2 | 10/2007 | Yeshurun | |
| 7,537,590 B2 | 5/2009 | Santini, Jr. et al. | |
| 7,578,954 B2 | 8/2009 | Gartstein et al. | |
| 7,658,728 B2 | 2/2010 | Yuzhakov | |

(Continued)

FOREIGN PATENT DOCUMENTS

| | | |
|---|---|---|
| WO | WO 00/74764 A1 | 12/2000 |
| WO | WO 02/091922 A1 | 11/2002 |

(Continued)

OTHER PUBLICATIONS

Co-pending U.S. Appl. No. 13/157,412, filed Apr. 27, 2011, by Russell Ross for "Nanopatterned Medical Device with Enhanced Cellular Interaction."

*Primary Examiner* — Kevin C Sirmons
*Assistant Examiner* — Brandy S Lee
(74) *Attorney, Agent, or Firm* — Douglas H. Tulley, Jr.

(57) ABSTRACT

The present invention includes a microneedle assembly having a support that includes a first surface and a second surface, the second surface further including a slanted surface. A plurality of microneedles are provided which project outwardly from the second surface of the support. A pathway through the microneedle assembly is formed and includes an aperture extending between the first surface of the support and the second surface of the support, a channel disposed on the exterior surface of at least one microneedle, the channel having a surface, the channel being in alignment with at least a portion of the aperture to form a junction through which fluids may pass.

20 Claims, 8 Drawing Sheets

(56) References Cited

U.S. PATENT DOCUMENTS

| | | |
|---|---|---|
| 7,753,888 B2 | 7/2010 | Mukerjee et al. |
| 7,785,301 B2 | 8/2010 | Yuzhakov |
| 7,901,387 B2 | 3/2011 | Stemme et al. |
| 8,062,253 B2 | 11/2011 | Nielsen et al. |
| 2002/0045859 A1 | 4/2002 | Gartstein et al. |
| 2003/0014014 A1 | 1/2003 | Nitzan |
| 2004/0072105 A1 | 4/2004 | Yeshurun et al. |
| 2004/0087992 A1 | 5/2004 | Gartstein et al. |
| 2004/0106904 A1 | 6/2004 | Gonnelli et al. |
| 2005/0143713 A1 | 6/2005 | Delmore et al. |
| 2005/0178760 A1 | 8/2005 | Chang et al. |
| 2007/0224253 A1 | 9/2007 | Franklin |
| 2007/0260201 A1 | 11/2007 | Prausnitz et al. |
| 2008/0102192 A1 | 5/2008 | Johnson et al. |
| 2008/0108958 A1 | 5/2008 | Carter et al. |
| 2008/0319392 A1 | 12/2008 | Angel et al. |
| 2009/0030365 A1 | 1/2009 | Tokumoto et al. |
| 2009/0093776 A1 | 4/2009 | Yue et al. |
| 2009/0118672 A1 | 5/2009 | Gonnelli et al. |
| 2010/0121307 A1 | 5/2010 | Lockard et al. |
| 2011/0021996 A1 | 1/2011 | Lee et al. |
| 2011/0144591 A1 | 6/2011 | Ross |
| 2011/0172609 A1 | 7/2011 | Moga et al. |
| 2011/0270221 A1 | 11/2011 | Ross |
| 2012/0109065 A1 | 5/2012 | Backes |
| 2012/0220980 A1 | 8/2012 | Ross |

FOREIGN PATENT DOCUMENTS

| | | |
|---|---|---|
| WO | WO 03/059431 A1 | 7/2003 |
| WO | WO 03/092785 A1 | 11/2003 |
| WO | WO 2006/062974 A2 | 6/2006 |
| WO | WO 2008/007906 A1 | 1/2008 |
| WO | WO 2009/049243 A2 | 4/2009 |
| WO | WO 2009/079712 A1 | 7/2009 |
| WO | WO 2011/135530 A2 | 4/2011 |
| WO | WO 2011/135531 A2 | 4/2011 |
| WO | WO 2011/135532 A2 | 4/2011 |
| WO | WO 2011/070457 A2 | 6/2011 |

* cited by examiner

FIG. 15A
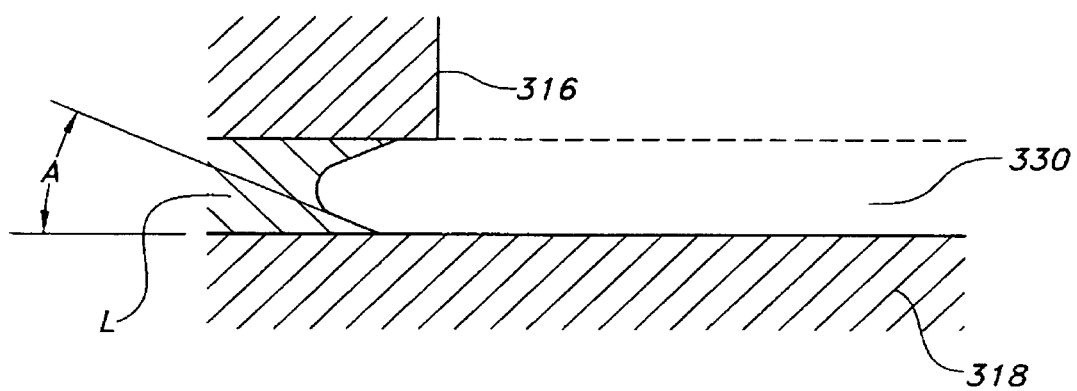
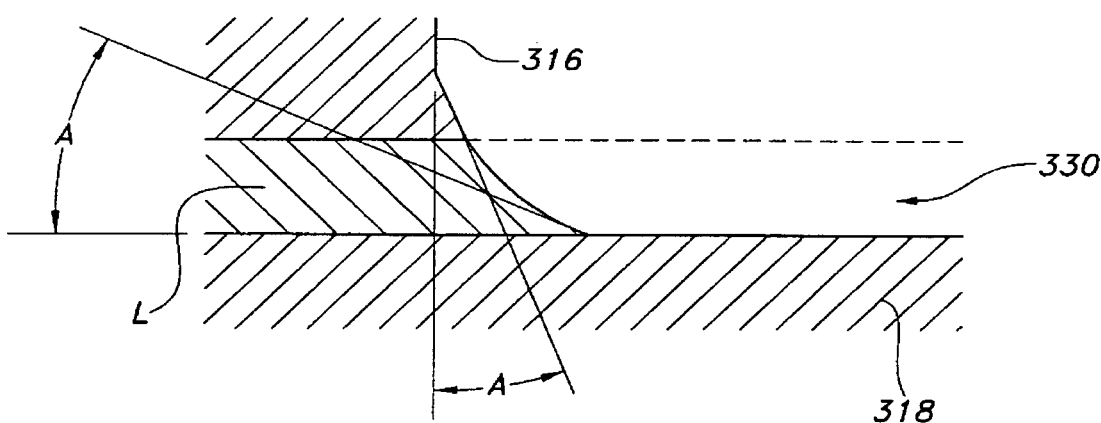
FIG. 15B

TRANSDERMAL DEVICE CONTAINING MICRONEEDLES

BACKGROUND OF THE INVENTION

The delivery of drugs to a patient is conventionally performed in a number of different ways. For example, intravenous delivery is by injection directly into a blood vessel; intraperitoneal delivery is by injection into the peritoneum; subcutaneous delivery is under the skin; intramuscular delivery is into a muscle; and oral delivery is through the mouth. One of the easiest methods for drug delivery, and for collection of body fluids, is through the skin. Skin is composed of the epidermis, including the stratum corneum, the stratum granulosum, the stratum spinosum, and the stratum basale, and the dermis, containing, among other things, the capillary layer. The stratum corneum is a tough, scaly layer made of dead cell tissue that extends around 10-20 microns from the skin surface and has no blood supply. Because of the density of this layer of cells, moving compounds across the skin, either into or out of the body, can be very difficult.

Current techniques for delivering local pharmaceuticals through the skin include methods that use needles or other skin piercing devices and methods that do not use such devices. Those methods that do not use needles typically involve: (a) topical applications, (b) iontophoresis, (c) electroporation, (d) laser perforation or alteration, (e) carriers or vehicles, which are compounds that modify the chemical properties of either the stratum corneum and/or the pharmaceutical, (f) physical pretreatment of the skin, such as abrasion of the stratum corneum (e.g., repeatedly applying and removing adhesive tape), and (g) sonophoresis, which involves modifying the barrier function of stratum corneum by ultrasound. Invasive procedures, such as use of needles or lances, can effectively overcome the barrier function of the stratum corneum. However, these methods suffer from several major disadvantages, including pain, local skin damage, bleeding, risk of infection at the injection site, and creation of contaminated needles or lances. These methods also usually require a trained administrator and are not suitable for repeated, long-term, or controlled use. Additionally, drug delivery through the skin has been relatively imprecise in both location and dosage of the pharmaceutical. Some of the problems include movement of the patient during administration, delivery of incomplete dosages, difficulties in administering more than one pharmaceutical at the same time, and difficulties in delivering a pharmaceutical to the appropriate part of the skin. Drugs have traditionally been diluted to enable handling of the proper dosages. This dilution step can cause storage as well as delivery problems. Thus, it would be advantageous to be able to use small, precise volumes of pharmaceuticals for quick, as well as long-term, delivery through the skin.

Microneedles have been proposed for this purpose. The microneedles typically have a hollow shaft, similar to larger conventional medical needles, so that drug compounds may be delivered through the hollow shaft. Various mechanisms have been employed to initiate the flow of the drug compound through such devices. U.S. Pat. No. 6,611,707 to Prausnitz et al., for example, describes a device having one or more drug reservoirs positioned over a housing that includes an array of hollow microneedles. A drug is delivered from the reservoir by applying a physical force, such as by pressing the top of the reservoir, to cause the drug to flow out through the microneedles. Unfortunately, due to their very small size, the hollow shafts of microneedles can break off when the physical force is applied. Further, the delivery of a drug compound that is initiated by such a physical force is sometimes too fast for achieving a controlled flow rate. U.S. Pat. No. 7,651,475 to Angel, et al. describes one attempt to overcome these problems by employing an actuator that pumps the drug compound between the reservoir and the body through the needles. While potentially helping to achieve a controlled flow rate, the use of such actuators (pumps) to induce flow is nevertheless cost prohibitive and overly complex, particularly when the product is intended for use by a person other than a medical professional.

As such, a need currently exists for a transdermal microneedle device that can easily deliver a drug compound without the need for active displacement mechanisms, such as pumps.

SUMMARY OF THE INVENTION

In one embodiment of the invention, a microneedle assembly is provided that includes a support having a first surface and a second surface, the second surface having a portion thereof that is slanted. A plurality of microneedles project outwardly from the second surface of the support, and at least one of the microneedles includes a base, a tip and an exterior surface. At least one of the microneedles may have a cross-sectional dimension ranging from about 1 micrometer to about 100 micrometers.

A pathway is formed and includes an aperture extending between the first surface of the support and the second surface of the support. A channel disposed on the exterior surface of at least one microneedle is in alignment with at least a portion of the aperture to form a junction through which fluids may pass. Some embodiments of the present invention may be formed such that two or more channels are formed in the exterior surface of the microneedle. The channel includes a surface which may be formed into various shapes, including for example a semi-circle or v-shape. The channel may also form a non-linear path along the exterior surface of the microneedle.

The junction is formed in the plane of the slanted surface proximate to the base of the microneedle. A first angle is formed between the slanted surface and the channel. While the value of the first angle may vary, in preferred embodiments the first angle is greater than 90 degrees and may be greater than 110 degrees or 120 degrees. In selected embodiments the first angle is less than 160 degrees.

The microneedle assembly described above may be included in a transdermal drug delivery device that also includes a drug delivery assembly having a reservoir for holding a drug compound, a rate control membrane that is in fluid communication with the reservoir, and a release member that is generally impermeable to the drug compound and is positioned adjacent to the rate control membrane and the first surface of the support of the microneedle assembly. In such embodiments, the release member may be configured to be at least partially separated from the rate control membrane and the support of the microneedle assembly when the drug delivery device is an active configuration.

The transdermal drug delivery device may also include an adhesive layer. In such embodiments, the reservoir may be positioned between the adhesive layer and the rate control membrane.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures described below.

FIGS. 15A and 15B are partial cross-sectional views of an embodiment of a microneedle assembly showing a fluid flowing down the channel proximate to the second surface.

Figure 1:
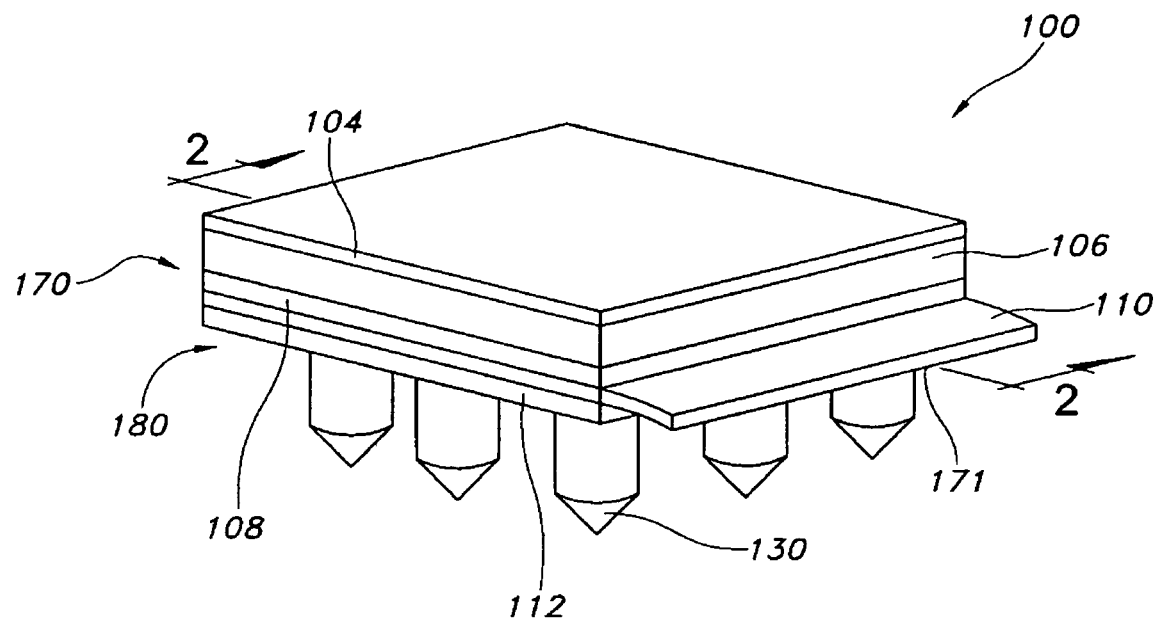
FIG. 1 is a perspective view of one embodiment of the transdermal drug delivery device of the present invention prior to delivery of a drug compound.

Repeat use of reference characters in the present specification and figures is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Figure 2:
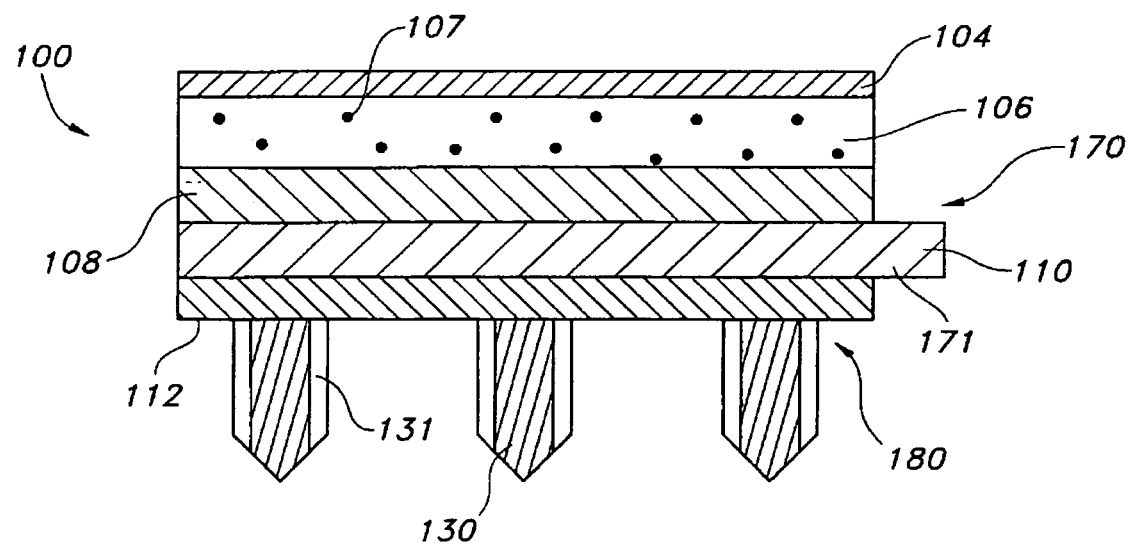
FIG. 2 is a cross-sectional view of the drug delivery device of FIG. 1.

Generally speaking, the present invention is directed to a transdermal drug delivery device, such as that depicted in FIG. 1 at 100 that can deliver a controlled volume of a fluidic drug compound to the skin. More particularly, FIGS. 1-2 show a transdermal drug delivery device 100 that contains a drug delivery assembly 170 and a microneedle assembly 180. The drug delivery assembly 170 includes a reservoir 106 positioned adjacent to a rate control membrane 108, such as described above. The drug delivery assembly 170 may also contain an adhesive layer 104 that is positioned adjacent to the reservoir 106. The microneedle assembly 180 includes a support 112 from which extends a plurality of microneedles 130 having channels 131. The layers of the drug delivery assembly 170 and/or the microneedle assembly 180 may be attached together if desired using any known bonding technique, such as through adhesive bonding, thermal bonding, ultrasonic bonding, etc.

Regardless of the particular configuration employed, the drug delivery device 100 also contains a release member 110 that is positioned between the drug delivery assembly 170 and the microneedle assembly 180. While the release member 110 may optionally be bonded to the adjacent support 112 and/or rate control membrane 108, it is typically desired that it is only lightly bonded, if at all, so that the release member 110 can be easily withdrawn from the drug delivery device 100. If desired, the release member 110 may also contain a tab portion 171 (FIGS. 1-2) that extends at least partly beyond the perimeter of the drug delivery device 100 to facilitate the ability of a user to grab onto the member and pull it in the desired direction.

Figure 3:
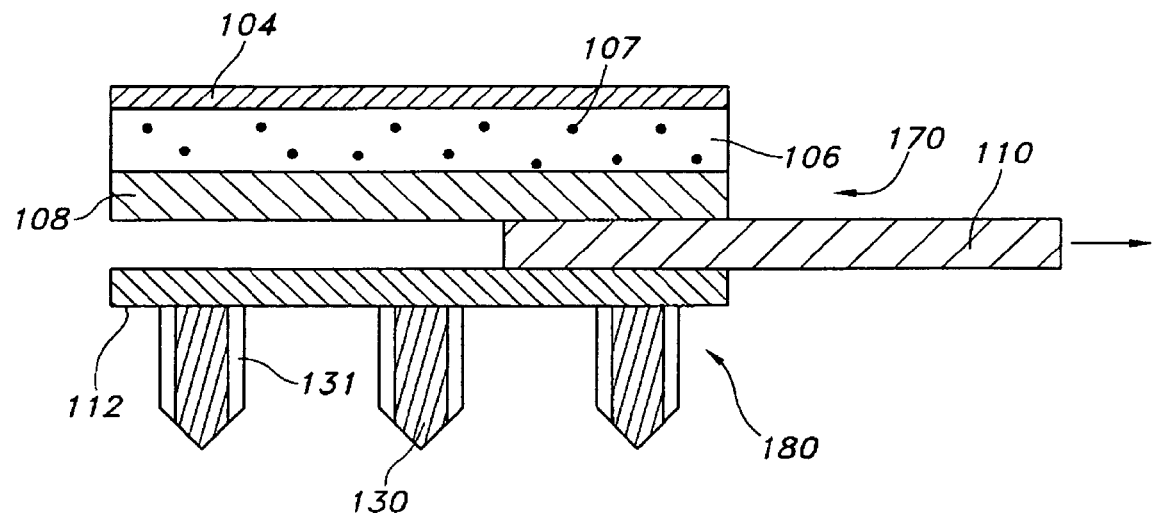
FIG. 3 is a cross-sectional view of the drug delivery device of FIG. 2 in which the release member is partially withdrawn from the drug delivery device.
Figure 4:
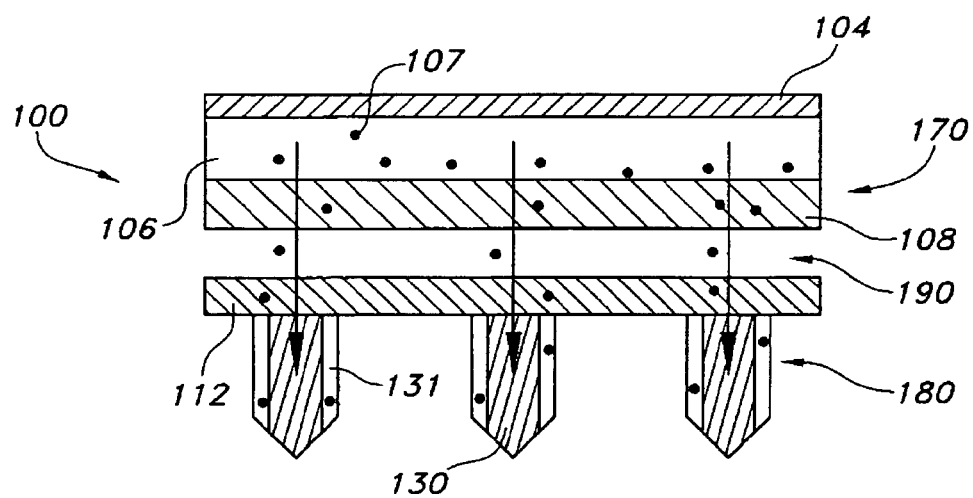
FIG. 4 is a cross-sectional view of the transdermal drug delivery device of FIG. 3 after removal of the release member and during use.

Prior to use and as shown in FIG. 1, the release member 110 acts as a barrier to the flow of the drug compound and thus inhibits premature leakage. In this manner, the transdermal drug delivery device can initially be provided in an "inactive" configuration in which the drug compound is securely retained. When it is desired to release the drug compound, the transdermal drug delivery device 100 can simply be activated by at least partially separating (e.g., detaching, rupturing, etc.) the release member 110 from the drug delivery assembly and the microneedle assembly. As depicted in FIG. 3, the release member 110 may be withdrawn from the transdermal drug delivery system to enable the drug compound to pass through the rate control membrane 108 and through the microneedle assembly 180 as shown in FIG. 4. The seal previously formed between the release member 110 and the aperture (not shown) of the support 112 is broken. In this manner, a drug compound 107 can begin to flow from the drug delivery assembly 170 and into the channels 131 of the microneedles 130 via the support 112. An exemplary illustration of how the drug compound 107 flows from the reservoir 106 and into the channels 131 is shown in FIG. 4. This allows the transdermal drug delivery device to be placed on the skin before activation, thereby limiting potential spillage of the drug compound.

Figure 5:
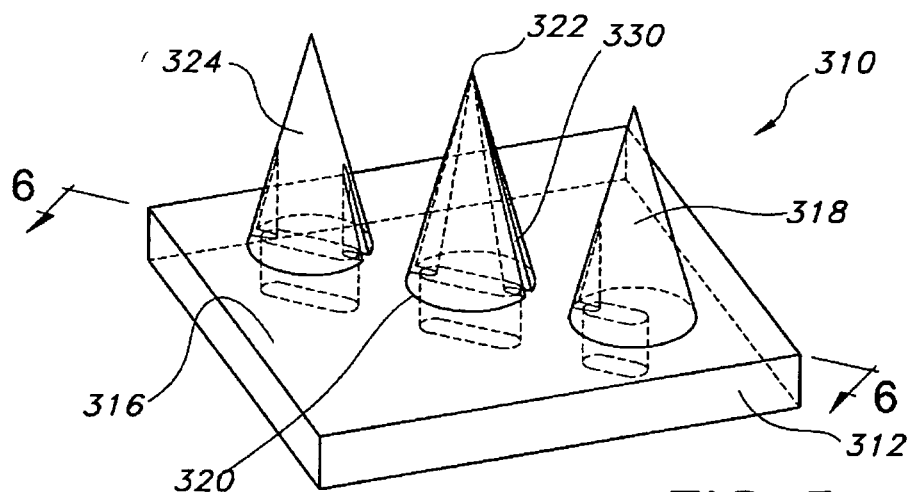
FIG. 5 is a perspective view of a microneedle assembly that may be employed in one embodiment of the transdermal drug delivery device of the present invention.
Figure 6:
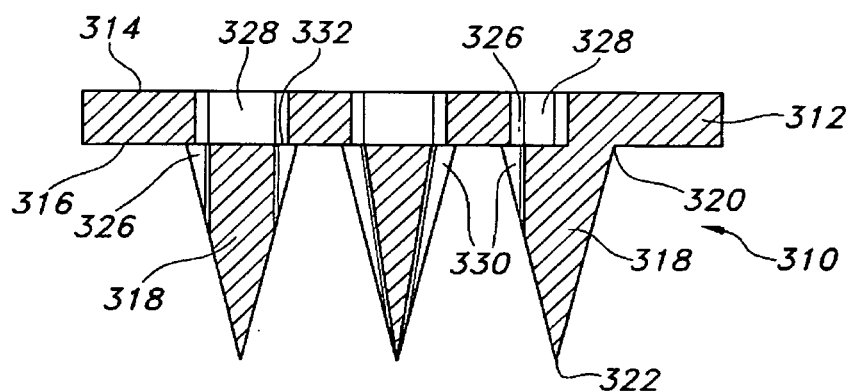
FIG. 6 is a cross-sectional view of the microneedle assembly of FIG. 13, taken along lines 5-5.

The microneedle assembly is shown in more detail in FIGS. 5-8. The microneedle assembly contains a plurality of microneedles that extend outwardly from a support. Referring to FIGS. 5-6, for example, one particular embodiment of a microneedle assembly 310 is shown in more detail that contains a plurality of microneedles 318 that extend from a support 312.

The size and shape of the microneedles 318 may vary as desired. For example, the microneedles 318 of FIGS. 5 and 6 have an overall conical shape. In alternative embodiments, however, the microneedles 318 may have an overall pyramidal shape or a cylindrical portion upon which is positioned a conical portion having a tip. The microneedles 318 may alternately have a rectangular cross-section.

The microneedle 318 typically includes a base 320, a tip 322 and an exterior surface 324. As shown in FIG. 5, the base 320 is the portion of the microneedle 318 that is proximate to the second surface 316 of the support 312. The tip 322 of the microneedle 318 is the point of the microneedle 318 that is furthest from the base 320. Although the tip 322 may be variously formed, it typically has a radius that is less than or equal to about 1 micrometer. Alternately and as shown in other figures, a single aperture may feed two or more separate channels 330.

Figures 7, 8:
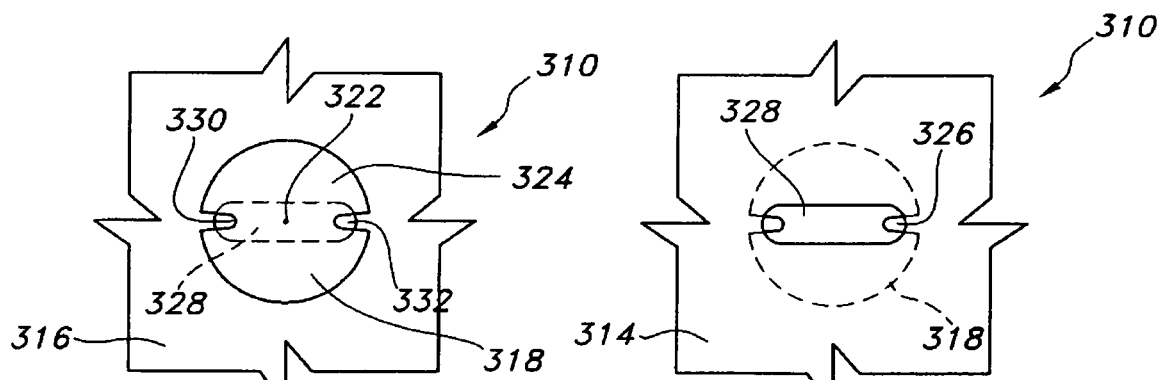
FIG. 7 is a top view of a microneedle assembly that may be employed in one embodiment of the transdermal drug delivery device of the present invention.
FIG. 8 is a bottom view of a microneedle assembly that may be employed in one embodiment of the transdermal drug delivery device of the present invention.

Referring again to FIGS. 5-6, for example, the illustrated microneedles 318 contain at least one channel 330. The channel may be located in a variety of different positions, such as in the interior of the channel, on an exterior surface, etc. In the embodiment illustrated in FIGS. 5-6, for example, the channel 330 is located on an exterior surface 324 of the microneedle 318. The cross-section of the channel 330, as shown in FIGS. 7 and 8, is substantially U-shaped. The channel 330 may also be arcuate or have any other configuration suitable for moving a substance therethrough, such as, for example, V-shaped or C-shaped. Regardless, a pathway 326 is formed by the channel 330 and the aperture 328, which meet at a junction 332 that is generally located in the plane of the second surface 316. Each microneedle 318 may deliver or extract drug compounds through the skin via the pathway 326, as depicted in FIG. 8. The pathway 326 enables the compound to flow from the first surface 314 through the aperture 328, the junction 332 and exiting into the channel 330. By enabling the compound to flow through the support 312 and directly into the channel 330, more precise control over the delivery location and the amount of substance delivered may be provided.

Alternate embodiments may include more channels if desired. The channel 330 may be variously positioned on the exterior surface 324, forming a substantially linear path from the base 320 towards the tip 322, or forming a winding or circuitous path along the exterior surface 324. In microneedles where two or more channels are present, the channels 330 may be variously spaced around the microneedle 318 in a symmetrical or asymmetrical manner.

For example, in some embodiments, the cross-sectional dimension of the channel typically ranges from about 1 micrometer to about 100 micrometers. The dimension may be constant or it may vary as a function of the length of the channel. The length of the channel may also vary to accommodate different volumes, flow rates, and dwell times for the drug compound. The cross-sectional area of the channel may also vary.

It should be understood that the number of microneedles 318 shown in the figures is for illustrative purposes only. The actual number of microneedles used in the transdermal drug delivery device 100 may, for example, range from about 500 to about 10,000.

FIG. 8 is a view looking at the first surface 314 of the microneedle assembly 310, which shows the junction 332 that is formed in the pathway 326 by the overlapping portions of the aperture 328 and the channel 330. FIG. 7 is a view looking down onto the second surface 316 of the microneedle 318, showing the junction 332 as seen from that portion of the microneedle assembly 310, which may be in contact with the skin of a user. The junction 332 may vary in area between pathways 326 on a given microneedle 318, and may vary between microneedles 318 on a given microneedle assembly 310. The area of the junction 332 may vary widely, and will depend on factors such as, for example, the diameter of the microneedle 318, the viscosity of the substance to be moved through the pathway 326 and the quantity of substance to be delivered. In certain embodiments, the area of the junction 332 at the second surface 316 is greater than or equal to about 100 square microns, although smaller areas may also be acceptable for use in the present invention. In other embodiments, the area of the junction 332 at the second surface 316 may be equal to about 150 square microns or greater.

In selected embodiments of the microneedle 318, the aperture 328 and channel 330 have sides that are not only coextensive with each other but may also be planar for at least some distance along the length of the pathway 326.

Regardless of their particular configuration, the microneedles generally define at least one channel that is in fluidic communication with at least a portion of the aperture of the support. The dimensions of the channel are specifically selected in the present invention to induce capillary flow of the drug compound. Capillary flow generally occurs when the adhesive forces of a fluid to the walls of a channel are greater than the cohesive forces between the liquid molecules.

The support 312 may be constructed from a rigid or flexible sheet of metal, ceramic, plastic or other material. The support 312 can vary in thickness to meet the needs of the transdermal drug delivery device, such as about 1000 micrometers or less, in some embodiments from about 1 to about 500 micrometers, and in some embodiments, from about 10 to about 200 micrometers.

The support includes at least one aperture 328 that extends through a first surface 314 and a second opposing surface 316 of the support 312. In the embodiment depicted in FIGS. 5 and 6, the microneedles 318 extend from the second surface 316, although in other embodiments the microneedles 318 may extend from the first surface 314 or elsewhere.

Figure 9:
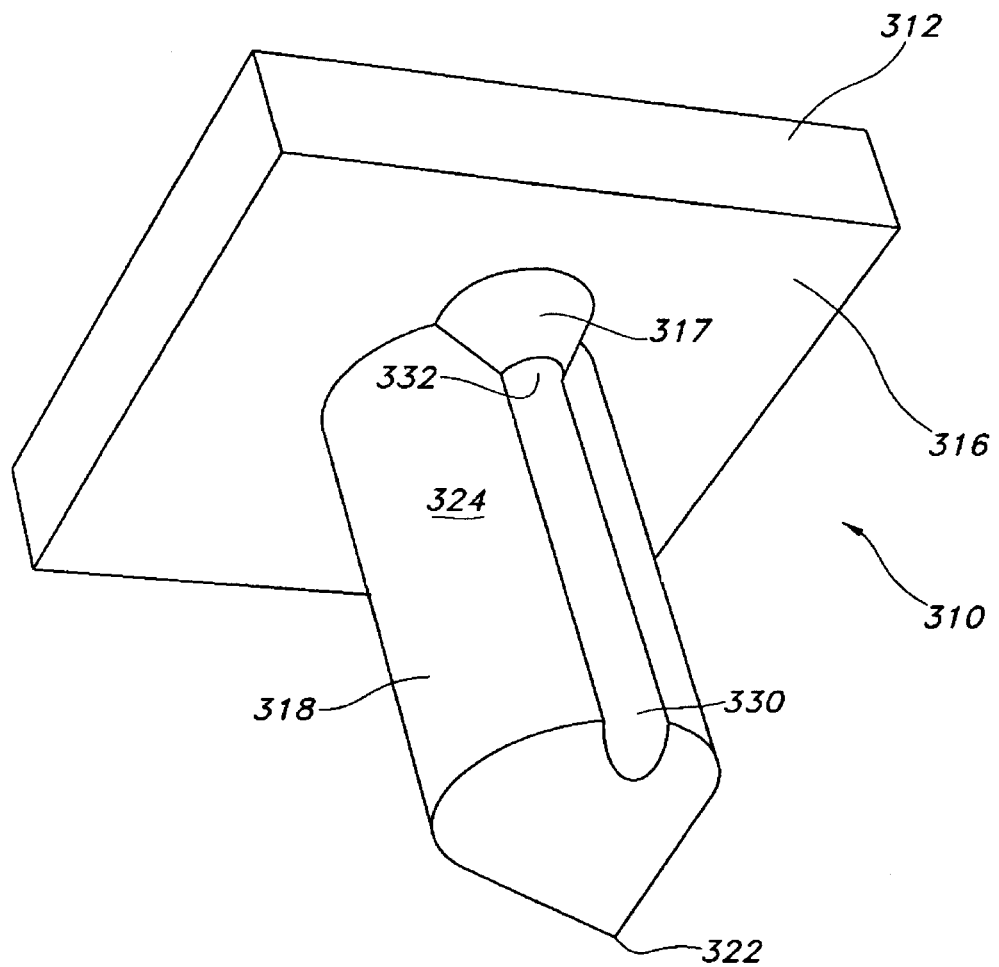
FIG. 9 is a perspective view of an embodiment of a microneedle assembly having a slanted surface.

The second surface 316 of the support 312 may also include a slanted surface 317, as shown in FIGS. 9-14. As shown in FIG. 9, the slanted surface 317 extends downwardly from the second surface 316 of the support 312. The slanted surface encircles the channel 330 and forms a contact angle alpha between the slanted surface and the exterior surface of the microneedle.

Figure 11:
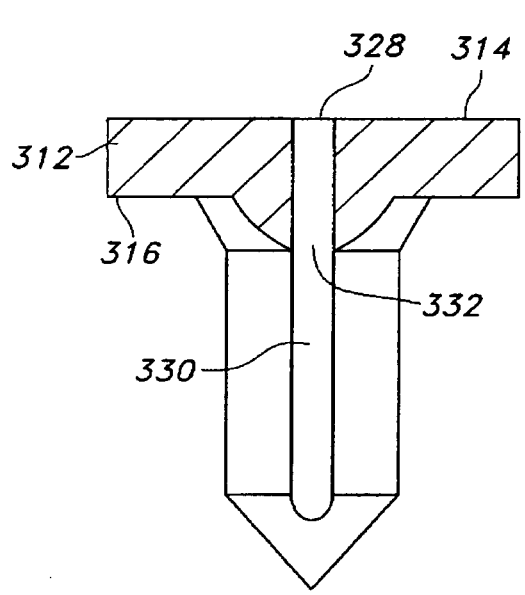
FIG. 11 is a partial cross-sectional view of the embodiment shown in FIG. 10.
Figure 10:
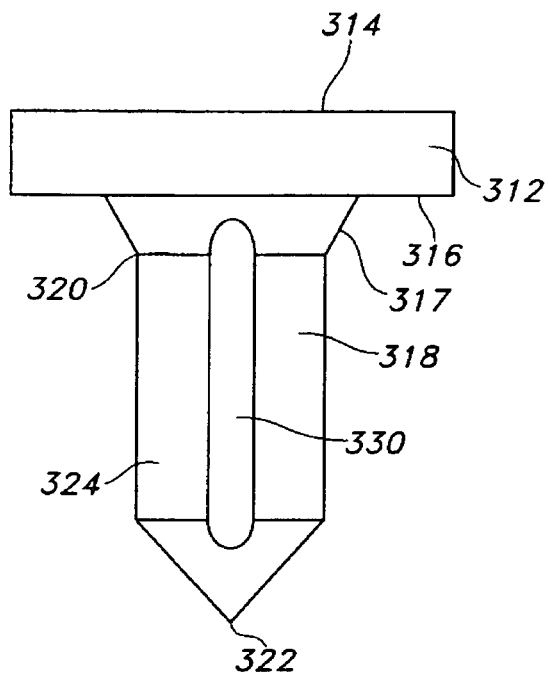
FIG. 10 is a perspective view of another embodiment of a microneedle assembly having a slanted surface.
Figure 12:
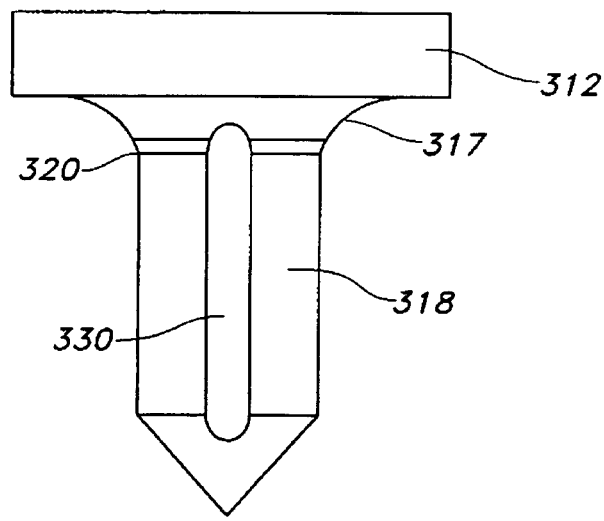
FIG. 12 is a perspective view of still another embodiment of a microneedle assembly having a slanted surface.

FIGS. 10, 11 and 12 depict alternate embodiments of the slanted surface 317 wherein the slanted surface is in contact with the full circumference of the base of the microneedle 318. FIG. 11 is a partial cross-sectional view of the embodiment of FIG. 10 showing the aperture 328, junction 332 and channel 330.

Figure 13:
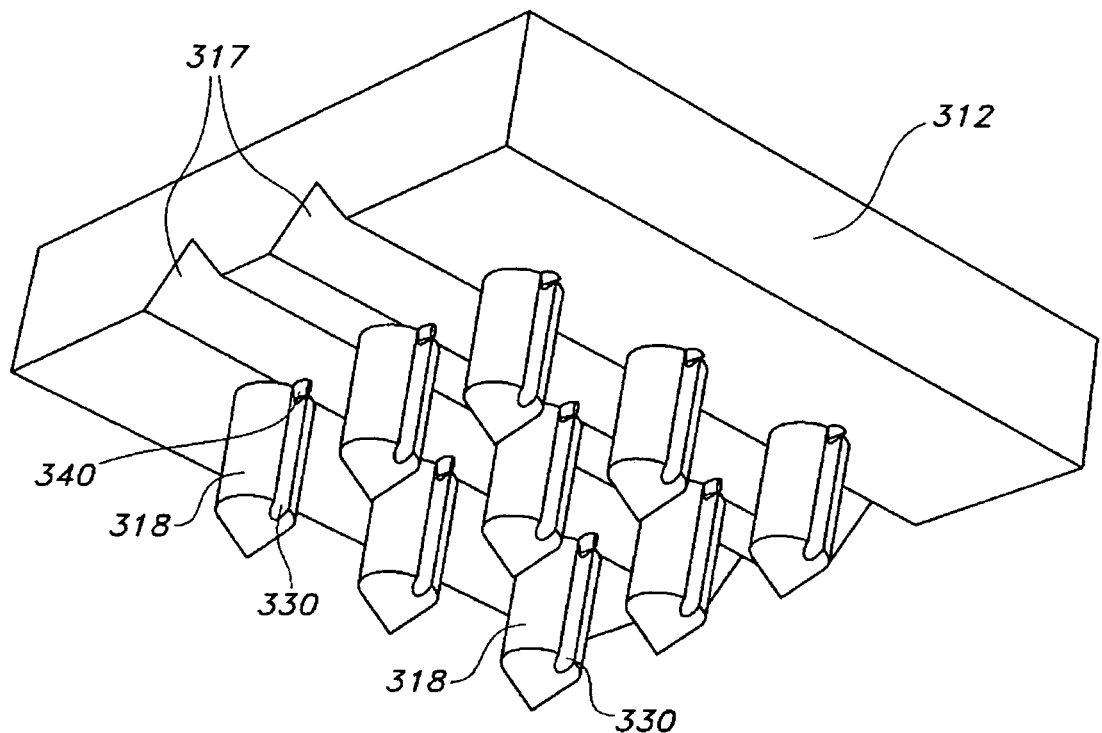
FIG. 13 is a perspective view of a different embodiment of a microneedle assembly of the present invention.
Figure 14:
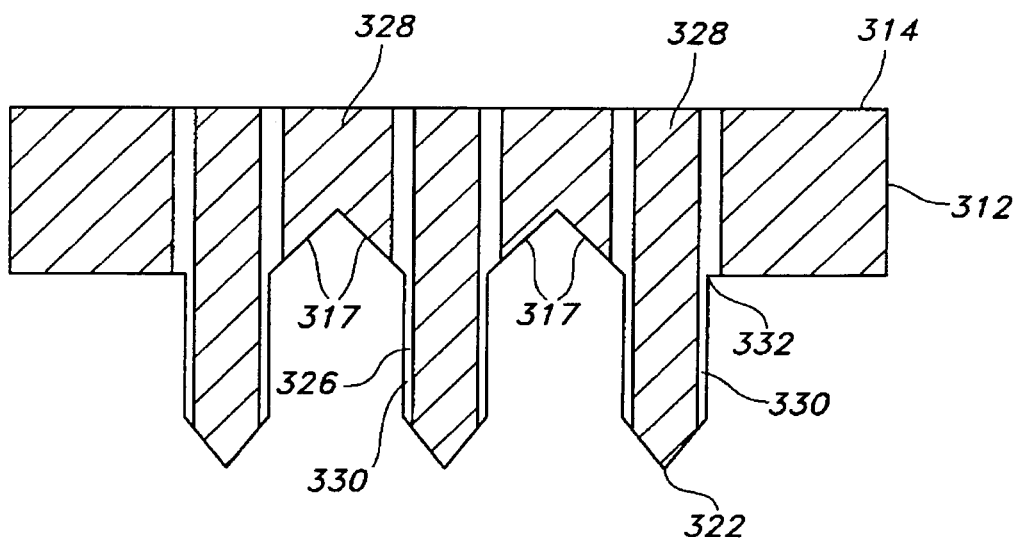
FIG. 14 is a partial cross-sectional view of the embodiment shown in FIG. 13.

An alternate embodiment of the present invention is shown in FIGS. 13 and 14 where the slanted surfaces 317 are formed as continuous grooves in the support 312. The slanted surfaces are proximate to the junction for each of the microneedles 318. As shown in FIG. 13, fluid 340 is passing out of the support 312 through the junction 332 and into the channel 330 of the microneedle 318. FIG. 14 is a partial cross-sectional view of the embodiment shown in FIG. 13, more clearly depicting the slanted surfaces 317 with respect to the pathway 326.

As depicted in FIGS. 15A and 15B, a liquid L is moving down the channel 330 in an embodiment of a microneedle which does not include a slanted surface 317. The angle "A" shown in FIGS. 15A-16B is the contact angle between the advancing liquid L and the channel. As the liquid reaches the edge of the second surface 316, the liquid L begins to spread outwardly along the second surface.

Figure 16A:
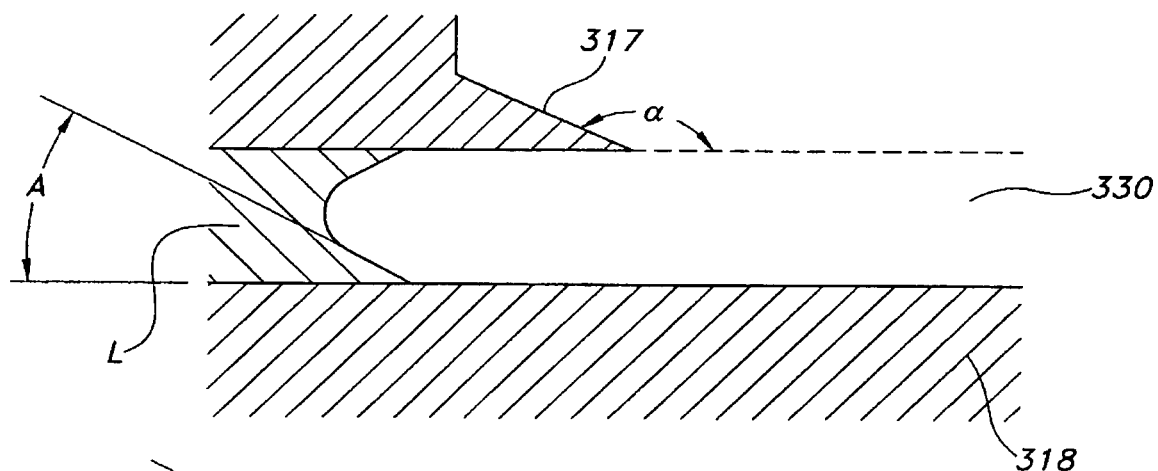
FIGS. 16A and 16B are partial cross-sectional views of an embodiment of a microneedle assembly showing a fluid flowing down the channel proximate to the slanted surface of the second surface.
Figure 16B:
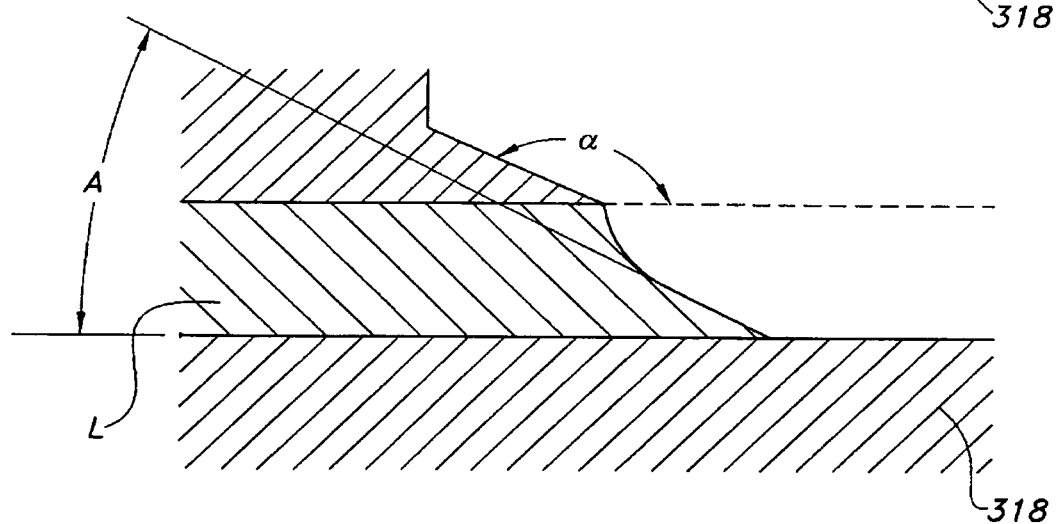

In contrast, FIGS. 16A and 16B depict an embodiment of a microneedle which includes a slanted surface 317. The angle alpha is depicted in FIGS. 16A-16B and is measured between the exterior surface of the slanted surface and the edge of the channel proximate to that second surface. The angle "alpha" (also referred to as the first angle) between the slanted surface and the channel is preferably greater than 90 degrees and in some embodiments may be greater than 110 degrees or 120 degrees. In selected embodiments, the first angle is less than 160 degrees. As the liquid L moves down the channel 330, the liquid tends to remain in the channel 330 rather than spread out and along the slanted surface 317. The slanted surface 317 helps to improve the delivery of the fluid down the channel of the microneedle.

In selected embodiments, the first angle may be selected to be less than the contact angle A of the fluid as measured or calculated by Young's equation:

$$\gamma_{SL} - \gamma_{SV} + \gamma_{LV} \cos(\theta) = 0$$

where gamma-sub-SL is the solid/liquid interface surface energy, gamma-sub-SV is the solid/vapor interface surface energy, and gamma-sub-LV is the liquid/vapor surface energy and theta is the contact angle between the three phases (Physical Chemistry of Surfaces, 5$^{th}$ edition by A. W. Adamson, John Wiley & Sons, New York, 1990, page 385).

The microneedles 318 are typically of a length sufficient to penetrate the stratum corneum and epidermis and into the dermis, but not sufficiently far into the dermis to contact nerve endings. In certain embodiments, the microneedles have a length (from their tip 322 to their base 320) of about 500 micrometers or less, in some embodiments from 1 to about 400 micrometers, and in some embodiments, from about 50 to about 350 micrometers.

The microneedles 318 may be arranged on the substrate in a variety of patterns, and such patterns may be designed for a particular use. For example, the microneedles may be spaced apart in a uniform manner, such as in a rectangular or square grid or in concentric circles. The spacing may depend on numerous factors, including height and width of the microneedles 318, as well as the amount and type of substance that is intended to be moved through the microneedles. While a variety of arrangements of microneedles is useful in the present invention, a particularly useful arrangement of microneedles 318 is a "tip-to-tip" spacing between microneedles of about 50 micrometers or more, in some embodiments about 100 to about 800 micrometers, and in some embodiments, from about 200 to about 600 micrometers. The microneedles 318 may be formed of various substances such as, for example, polymers, ceramics and metals.

While numerous processes may be used to manufacture microneedles according to the present invention, a suitable production system is MEMS (Micro-Electro-Mechanical Systems) technology and microfabrication processes. MEMS is capable of forming micromechanical and other elements such as semiconductors on a single silicon substrate using microfabrication processes such as etching, micromachining or other processes. The support 312 may be manufactured from silicon, the microneedles being subsequently formed by a microetching process. Micromolding techniques may also be used to form the microneedles 318 and support 312.

As indicated above, the drug delivery assembly of the transdermal transdermal drug delivery device contains a reservoir that can initially retain a drug compound. The term "reservoir" generally refers to a designated area or chamber configured to retain a fluidic drug compound. The reservoir may be an open volume space, gel, solid structure, etc. Nevertheless, in most embodiments, the reservoir is a solid matrix through which the drug compound is capable of flowing. The selection of the desired materials for the matrix typically depends on the solubility and diffusivity of the target drug compound and the time during which release is sought. In one embodiment, for example, the solid matrix is generally impermeable to the compound, and the material used to form the matrix is selected so that the drug compound is able to diffuse therethrough. In other embodiments, however, the solid matrix may be permeable or semi-permeable to the drug compound so that it can simply flow through its pores. Examples of such solid matrices include porous fiber webs (e.g., woven or nonwoven), apertured films, foams, sponges, etc. Regardless of its particular form, polymeric materials are often used to form the solid matrix, such as silicones, acrylic resins, acetate copolymers (e.g., ethylene vinyl acetate), plasticized polyvinyl acetate/polyvinyl chloride resins, plasticized hydrolyzed polyvinyl alcohol, rubber-based adhesives (e.g., polyisobutylenes extended with a solvent such as mineral oil), plasticized polyvinyl chloride, polyethylene glycols and polypropylene glycols of varying molecular weights, cellulose esters, polyolefins; etc.

There is no particular limitation to the drug compounds that may be retained within the reservoir and employed in the transdermal drug delivery device 100 of the present invention. Suitable compounds may include, for instance, proteinaceous compounds, such as insulin, immunoglobulins (e.g., IgG, IgM, IgA, IgE), TNF-α, antiviral medications, etc.; polynucleotide agents, such as plasmids, siRNA, RNAi, nucleoside anticancer drugs, vaccines, etc.; small molecule agents, such as alkaloids, glycosides, phenols, etc.; anti-infection agents, hormones, drugs regulating cardiac action or blood flow, pain control; and so forth.

Due to its controlled capillary flow, the transdermal drug delivery device 100 of the present invention may be particularly beneficial in delivering high molecular weight drug compounds that were previously difficult to deliver via transdermal delivery. The term "high molecular weight" generally refers to compounds having a molecular weight of about 1 kiliDalton ("kDa") or more, in some embodiments about 10 kDa or more, in some embodiments about 20 kDa to about 250 kDa, and in some embodiments, from about greater than about 40 kDa to about 150 kDa. Examples of such high molecular weight compounds include protein therapeutics, which refers to any biologically active proteinaceous compound including, without limitation, natural, synthetic, and recombinant compounds, fusion proteins, chimeras, and so forth, as well as compounds including the 20 standard amino acids and/or synthetic amino acids. In one particular embodiment, the transdermal drug delivery device 100 may be utilized in treatment of a chronic condition, such as rheumatoid arthritis ("RA"), to deliver a steady flow a drug to a subject in need thereof. Through utilization of the transdermal drug delivery device of the present invention, RA drugs can be delivered at a steady concentration over a sustained period. The transdermal drug delivery device 100 can prevent the initial burst of concentration common when utilizing previously known methods for delivery of RA drugs, including oral delivery and injection.

If desired, the transdermal drug delivery device may employ a plurality of reservoirs for storing multiple materials for delivery. The reservoirs may be positioned adjacent to each other, either in a vertical or horizontal relationship. For instance, a first reservoir may contain a drug compound and a second reservoir may contain an excipient (e.g., delivery vehicle, such as alcohols, water, etc.; buffering agents; and so forth). In one particular embodiment, for example, the first reservoir may contain a lyophilized powder of the drug compound (e.g., RA drug) and the second reservoir may contain an aqueous solution for reconstituting the powder. Alternatively, multiple reservoirs may be employed that each contains a drug compound. Regardless, the different materials may be mixed prior to delivery.

The drug delivery assembly also contains a rate control membrane that is in fluid communication with the drug reservoir. The rate control membrane can help slow down the flow rate of the drug compound upon its release. Specifically, fluidic drug compounds passing from the drug reservoir to the microneedle assembly may experience a drop in pressure that results in a reduction in flow rate. If this difference is too great, some backpressure may be created that can impede the flow of the compound and potentially overcome the capillary pressure of the fluid through the microfluidic channels. Thus, the use of the rate control membrane can ameliorate this difference in pressure and allow the drug compound to be introduced into the microneedle at a more controlled flow rate. The particular materials, thickness, etc. of the rate control membrane can vary based on multiple factors, such as the viscosity of the drug compound, the desired delivery time, etc.

The rate-controlling membrane may be fabricated from permeable, semi-permeable or microporous materials that are known in the art to control the rate of drug compounds and having a permeability to the permeation enhancer lower than that of drug reservoir. For example, the material used to form the rate control membrane may have an average pore size of from about 50 nanometers to about 5 micrometers, in some embodiments from about 100 nanometers to about 2 micrometers, and in some embodiments, from about 300 nanometers to about 1 micrometer (e.g., about 600 nanometers). Suitable membrane materials include, for instance, fibrous webs (e.g., woven or nonwoven), apertured films, foams, sponges, etc., which are formed from polymers such as polyethylene, polypropylene, polyvinyl acetate, ethylene n-butyl acetate and ethylene vinyl acetate copolymers. A particularly suitable membrane material is available from Lohmann Therapie-Systeme.

If desired, the drug delivery assembly may contain additional layers or materials that provide various benefits to the resulting transdermal drug delivery device. In one embodiment, for example, the assembly includes an adhesive layer that can help facilitate the attachment of the transdermal drug delivery device 100 to a user's skin during use. Although not required, the adhesive layer is often disposed over the reservoir. The adhesive layer typically employs an adhesive coated onto a backing material. The backing may be made of a material that is substantially impermeable to the drug compound, such as polymers, metal foils, etc. Suitable polymers may include, for instance, polyethylene terephthalate, polyvinylchloride, polyethylene, polypropylene, polycarbonate, polyester, and so forth. The adhesive may be a pressure-sensitive adhesive as is known in the art. Suitable adhesives may include, for instance, solvent-based acrylic adhesives, solvent-based rubber adhesives, silicone adhesives, etc.

As indicated above, a release member is initially positioned adjacent to the microneedle assembly and the drug delivery assembly so that it is adjacent to the support of the microneedle assembly and the rate control membrane of the drug delivery assembly. It should be understood, however, that the release layer need not contact such layers, and that other layers may be in fact be positioned between the release member and the support and/or rate control membrane. Regardless, the release member is made of a material that is substantially impermeable to the drug compound, such as a polymeric material, metal, etc. The material is also desirably hydrophobic. Suitable polymeric materials may include, for instance, polyethylene terephthalate, polyvinylchloride, polyethylene, polypropylene, polycarbonate, polyester, metal foils, and so forth. Because it is generally impermeable, the release member can initially seal the aperture in the support and thus limit the flow of the drug compound therethrough. When it is desired to use the transdermal drug delivery device, a force may be applied by the user to at least partially separate the release member, thereby breaking the seal.

The separation of the release member may be accomplished in a variety of ways. For instance, a portion of the release member may simply be ruptured. Any of a variety of known techniques for forming a rupturable layer may be employed in the present invention. In one embodiment, for example, the release member may be bonded about its perimeter. The strength of the bonds may exceed the tensile strength of the release member so that when a tensile force is applied, an inner portion of the substrate ruptures while the bonded perimeter remains in tact.

In alternative embodiments, separation may be accomplished through the partial or complete detachment of the release member. For example, referring to FIGS. 1-6, one embodiment of a release member is shown that is configured to be detached from the transdermal drug delivery device to initiate the flow of the drug compound The embodiments illustrated above contain only a single release member. However, it should be understood that additional release members may be employed in the present invention to accomplish a variety of different purposes.

While the invention has been described in detail with respect to the specific embodiments thereof, it will be appreciated that those skilled in the art, upon attaining an understanding of the foregoing, may readily conceive of alterations to, variations of, and equivalents to these embodiments. In addition, it should be noted that any given range presented herein is intended to include any and all lesser included ranges. For example, a range of from 45-90 would also include 50-90; 45-80; 46-89 and so forth. Accordingly, the scope of the present invention should be assessed as that of the appended claims and any equivalents thereto.

What is claimed is:

1. A microneedle assembly comprising:
a support comprising a first outer surface and a second outer surface, the second outer surface having sections that are parallel and sections that are slanted relative to the first surface;
a plurality of microneedles projecting outwardly from the second outer surface of the support, the microneedles comprising a base, a tip and an exterior surface;
a pathway comprising
an aperture extending through the interior of the support between the first outer surface of the support and the second outer surface of the support;
a channel disposed on the exterior surface of the plurality of microneedles, the channel having a surface, the channel being in end-to-end alignment with at least a portion of the aperture to form a junction through which fluids may pass, the junction being formed in the plane of the slanted section of the second outer surface of the support proximate to the base of the microneedle; and
a first angle formed between the slanted section of the second outer surface and the surface of the channel, the first angle being greater than 90 degrees.

2. The microneedle assembly as claimed in claim 1, the first angle being less than 160 degrees.

3. The microneedle assembly as claimed in claim 1, the first angle being greater than 110 degrees.

4. The microneedle assembly as claimed in claim 1, the first angle being greater than 120 degrees.

5. The microneedle assembly as claimed in claim 4, the first angle being greater than 135 degrees.

6. The microneedle assembly as claimed in claim 1, wherein the plurality of microneedles have at least two channels on the exterior surface.

7. The microneedle assembly as claimed in claim 1, the channel forming a non-linear path on the exterior surface of the microneedle.

8. The transdermal delivery device of claim 1 wherein the base of the microneedle is cylindrical or rectangular in shape.

9. The transdermal delivery device of claim 8 wherein the tip of the microneedle has a conical or pyramidal shape.

10. The transdermal delivery device of claim 1 wherein the cross-sections of the apertures and channels are coextensive at the junctions and further wherein the fluidic pathways comprise a linear pathway.

11. The transdermal delivery device of claim 1 wherein the junctions associated with at least two distinct microneedles are formed in the plane of a single continuous slanted section of the second outer surface of the support.

12. A transdermal drug delivery device comprising:
(i) a microneedle assembly comprising,
(a) a support comprising a first outer surface and a second outer surface, the second outer surface having sections that are parallel and sections that are slanted relative to the first outer surface;
(b) a plurality of microneedles projecting outwardly from the second outer surface of the support, the microneedles comprising a base, a tip and an exterior surface;
(c) fluidic pathways comprising
a plurality of apertures extending through the interior of the support between the first outer surface of the support and the second outer surface of the support,
at least one channel disposed on the exterior surface of at least one microneedle, the channel having a surface, the channel being in end-to-end alignment with at least a portion of one of said apertures to form a junction through which fluids may pass, the junction being formed in the plane of the slanted section of the second outer surface of the support proximate to the base of the microneedles wherein a first angle formed between the slanted section of the second surface and the surface of the channel is greater than 90 degrees;
(ii) a drug delivery assembly comprising
(a) a reservoir for holding a drug compound,
(b) a rate control membrane that is in fluid communication with the reservoir positioned between the reservoir and the first outer surface of the support, and
(iii) a release member that is impermeable to the drug compound and positioned adjacent to the rate control membrane of the drug delivery assembly and the first surface of the support of the microneedle assembly, wherein the release member is configured to be at least partially separated from the rate control membrane of the drug delivery assembly and the support of the microneedle assembly when drug delivery device is an active configuration.

13. The transdermal drug delivery device of claim 12, wherein the drug delivery assembly further comprises an adhesive layer, the reservoir being positioned between the adhesive layer and the rate control membrane.

14. The transdermal drug delivery device of claim 12, wherein the release member is positioned between the rate control membrane and the support.

15. The transdermal drug delivery device as claimed in claim 12, the first angle being less than 160 degrees.

16. The transdermal drug delivery device as claimed in claim 12, wherein the microneedles have at least two channels.

17. The transdermal drug delivery device as claimed in claim 12, the channel forming a non-linear path on the exterior surface of the microneedle.

18. The transdermal delivery device as claimed in claim 12, the first angle being greater than 110 degrees.

19. The transdermal delivery device of claim 12 wherein the rate control membrane comprises a porous material having an average pore size of between about 50 nanometers to about 5 micrometers.

20. The transdermal delivery device of claim 12 wherein the release member has an exposed tab that extends at least partly beyond the perimeter of the microneedle assembly and further wherein the release member is configured to be at least partially separated from the rate control membrane of the drug delivery assembly and the support of the microneedle assembly when the exposed tab of the release member is pulled.

* * * * *